United States Patent [19]
Herbert et al.

[11] Patent Number: 5,552,268
[45] Date of Patent: Sep. 3, 1996

[54] METHOD FOR MEASURING TOTAL BODY TISSUE IRON STORES

[75] Inventors: Victor D. Herbert, New York; Spencer Shaw, Larchmont, both of N.Y.; Elizabeth Jayatilleke, Englewood, N.J.

[73] Assignee: Quixote Associates, Inc., Katonah, N.Y.

[21] Appl. No.: 512,466

[22] Filed: Aug. 8, 1995

Related U.S. Application Data

[63] Continuation-in-part of Ser. No. 283,598, Aug. 1, 1994.

[51] Int. Cl.$^6$ ........................................ C12Q 1/00
[52] U.S. Cl. .................... 435/4; 435/6; 435/7.9; 435/961; 435/962; 436/518; 436/523; 436/529; 436/533; 436/538; 436/548; 436/84
[58] Field of Search ............... 435/4, 7.1, 6, 7.9, 435/961, 962; 436/518, 523, 529, 533, 538, 548, 84, 175

[56] References Cited

U.S. PATENT DOCUMENTS

| | | | |
|---|---|---|---|
| 4,278,652 | 7/1981 | Niemann et al. | 424/1 |
| 4,833,322 | 5/1989 | Forster et al. | 250/288 |
| 4,889,125 | 12/1989 | Doddrell et al. | 128/653 |
| 4,961,970 | 10/1990 | Siedel et al. | 436/84 |
| 5,017,498 | 5/1991 | Fossati et al. | 436/84 |
| 5,102,626 | 4/1992 | Beach | 422/99 |
| 5,200,270 | 4/1993 | Ishida et al. | 428/403 |
| 5,219,760 | 6/1993 | Herrmann et al. | 436/84 |
| 5,322,682 | 6/1994 | Bartzokis et al. | 424/9 |

OTHER PUBLICATIONS

The American Heritage Dictionary 2nd College Edition 1982 Houghton Mifflin Company p. 624.
J. Gutteridge et al, "Superoxide–Dependent Formation of Hydroxyl Radicals in the presence of iron salts," Biochem. J. (1981) vol. 199, pp. 263–265.
P. Pootrakul et al, "Quantitation of Ferritin Iron in Plasma, an Explanation for Non–Transferrin Iron," Blood (Apr. 1988) vol. 71, No. 4; pp. 1120–1123.
N. Tietz (ed.), Textbook of Clinical Chemistry, 1986 W. B. Saunders Company, pp. 1577–1584, 914–915.
F. Zuyderhoudt et al., "A Method for Measurement of Liver Iron Fractions in Needle Biopsy Specimens and Some Results in Acute Liver Disease," Clinica Chimica Acta, 86 (1978):313–321.
F. Zuyderhoudt et al., "On the Iron Content of Human Serum Ferritin, Especially in Acute Viral Hepatitis and Iron Overload" Clinica Chimica Acta. 90 (1978) 93–99.

*Primary Examiner*—Carol A. Spiegel
*Attorney, Agent, or Firm*—Elliot M. Olstein; Gregory D. Ferraro

[57] ABSTRACT

A non-invasive method to measure total body tissue iron stores comprising recovering iron released from total ferritin contained in a body fluid sample derived from a host, measuring the ferritin-iron in the total ferritin and thereby determining total body tissue iron stores. Such an assay is utilized for diagnosing negative iron balance as well as positive iron balance, wherein the latter promotes cancer, coronary artery disease, atherosclerosis, and hepatic failure among other diseases, as well as the susceptibility to such diseases.

19 Claims, No Drawings

METHOD FOR MEASURING TOTAL BODY TISSUE IRON STORES

CROSS-REFERENCES TO RELATED APPLICATIONS

This application is a continuation-in-part of U.S. patent application Ser. No. 08/283,598 filed Aug. 1, 1994. The present invention relates to a method for determining the total body tissue iron stores in a host. More particularly, the present invention relates to a method of measuring the amount of iron contained in the total ferritin isolated from a body fluid sample derived from a host and further measuring the part which is holoferritin and the part which is apoferritin.

BACKGROUND OF THE INVENTION

Total body tissue iron stores are an important diagnostic indicator to the health professional of the presence of diseased states or a susceptibility to diseased states in an individual.

Body iron is both a necessary component for cellular metabolism and a highly damaging agent when present in excess. For example, iron leashed to protein is an essential element in all cell metabolism and growth, but is toxic when unleashed (Herbert V., et al., *Stem Cells*, 92:1502–1509 (1994)). Because of its ability to switch back and forth between ferrous and ferric oxidation states, iron is both a strong biological oxidant and reductant. Ferric iron or $Fe^{3+}$ is a relatively harmless form of iron. However, ferrous iron or $Fe^{2+}$ plays a significant role in the generation of oxygen radicals, excess of which have been proven to be extremely harmful to the health of an individual.

The human diet contains a multitude of natural chemicals which are carcinogens and anti-carcinogens, many of which act by generating oxygen radicals, which initiate degenerative processes related to cancer, heart disease and aging (Ames, B., *Science*, 221:1256–1264 (1993)). Among these many dietary chemicals are many redox agents, including vitamin C and beta carotene.

Free radical damage is produced primarily by the hydroxyl radical (.OH). Most of the .OH generated in vivo comes from iron-dependent reduction of $H_2O_2$ (Halliwell, B., *Archives of Biochemistry and Biophysics*, 246(2):501–514 (1986)), and supporting too much iron as a free radical-generating culprit leads to a risk of cancer. High total body tissue iron stores promotes diabetes, impotence, cancer, heart disease and liver disease (Stevens, R. G., et al., *N. Engl. J. Med.*, 319:1047–1052 (1988).

When ferrous iron reduces $H_2O_2$ to generate .OH, it becomes ferric iron. Vitamin C (ascorbic acid) converts ferric iron back to ferrous iron, itself becoming oxidized ascorbic acid, thus allowing another cycle of .OH generation from renewed ferrous iron (Aisen, P. et al., *Int. Rev. Exp. Path*, 31:1–46 (1990)).

The importance of iron in tumor growth is illustrated by the fact that iron deficiency slows the progression of malignancy (Hann, H. W. L. et al., *Cancer Res.*, 48:4168–4174 (1988)). Catalytic iron free radical generation mutates DNA and promotes cancer. Conversely, too much catalytic iron within a cancer cell will destroy it.

Accordingly, it is a vital necessity to be able to determine the quantity of iron in the body. It is also important to have access to a non-invasive diagnostic assay which provides a quick and accurate way to determine total body tissue iron stores.

The body has developed a system to prevent against these undesirable effects of iron in the body.

Ferritin is an iron-containing spherical protein of 24 repeating subunits and a molecular weight of approximately 460,000. Ferritin exists in many different forms, all of which perform various roles relating to delivering, storing and controlling iron. Apoferritin contains no iron and is generated by the body in response to inflammation, disease or an iron challenge, for example, an iron overload.

In response to disease, cells of the reticulo-endothelial system manufacture a series of proteins called acute phase reactants, which aid in scavenging bacteria, viruses and any other foreign particles. Apoferritin is one of these acute phase reactants. The intracellular generation of apoferritin is a cytoprotective antioxidant stratagem of reticulo-endothelial cells (Balla, J. et al., *Trans. Assoc. Am. Phys..*, 105: (in press) (1993)). It is probably also a cytoprotective antioxidant stratagem of all proliferating cells, including cancer cells, since ferritin is elevated in acute leukemia and many other cancers, including solid tumors, particularly when metastatic (Voest, E. E., *University of Utrecht, The Netherlands; June*, 1993 (*Thesis*)). These serum ferritin levels may actually rise with chemotherapy. This hyperferritinemia is often mainly apoferritin generated in the tumor cells, but malignancy, like chronic inflammation, also causes generation of apoferritin in the cells of the reticuloendothelial system (Worwood, M., Iron in Biochemistry and Medicine, Volume II, Academic Press, 224–233 (1980) and Herbert V., *J. Am. Diet Assoc.*, 92:1502–1509 (1992)). It is important that, although the literature almost exclusively uses the word "ferritin", what is generated within cells in response to an iron challenge is apoferritin, free of iron, which can then bind iron that would otherwise be cell-damaging. It binds and stores iron and prevents its uncontrolled release. The iron in it is in an iron core of ferric-oxide phosphate and, when the core is fully saturated, may consist of over 20% iron. About ⅔ of the body storage iron is in ferritin, with the remaining storage iron contained in hemosiderin, a denatured ferritin. One ferritin molecule is capable of binding up to a maximum of 4500 atoms of iron.

Ferritin which contains iron is called holoferritin. Holoferritin is not an acute phase reactant and, unlike apoferritin, the number of holoferritin molecules remains constant in the presence of inflammation or disease. What ferritin actually means, therefore, is the total of both apoferritin and holoferritin.

Circulating ferritin co-exists with serum transferrin (Tf) which is an iron delivery protein, for which there are receptors on every cell which needs iron. Transferrin absorbs iron from foodstuffs and delivers it to all cells which need iron as part of their normal metabolism. An example is red blood cells which need iron for the heme group of hemoglobin. Another example is muscle cells which use iron for the production of myoglobin. Tf delivers excess iron to storage cells which encapsulate the iron into holoferritin. Tf is a reverse acute phase reactant which means that in response to a disease state or inflammation the number of Tf molecules is reduced.

The holoferritin molecule can be analogized to a porous golf ball within which ferric iron is contained and is unable to escape. However, when ferric iron is reduced to ferrous iron by, for example, vitamin C or another reducing agent, ferrous iron is able to escape the ferritin molecule and is released into the circulation to generate harmful free radicals.

A diagnostic test for measuring total body tissue iron stores is important for diagnosing iron status, since either positive or negative iron balance promotes disease, susceptibility to disease, and aids a medical professional in diagnosing a patient and instructing the patient on the type of diet to maintain, in terms of iron content and iron availability for absorption. This is critical for those heterozygous for a gene promoting enhanced absorption, which can result in iron overload. Over 10% of Americans have an HLA-linked gene for enhanced iron absorption and about 30% of Africans have a non-HLA linked gene for enhanced iron absorption. Thus, in the United States, there is a large population at risk that is not identifiable by HLA typing, but is identifiable by the method of the present invention.

In people with genetically enhanced iron absorption, vitamin C supplements can only do harm. Vitamin C not only enhances iron absorption, but, worse, both releases catalytic iron from ferritin and drives the repetitive reduction of ferric to ferrous iron, with repetitive generation of more and more free radicals.

Current tests available for measuring total tissue iron stores are inaccurate because they only measure the number of molecules of ferritin protein, both apoferritin and holoferritin combined, and provide no information as to how much iron that ferritin protein carries. This is a crucial flaw since ferritin can carry no iron or up to 4500 atoms of iron. By convention, measurement of total ferritin protein is referred to as measurement of serum "ferritin".

In patient's with no illness or inflammation, "serum ferritin" generally provides an accurate reflection of body storage iron. A medical professional can measure the isolated total serum ferritin (µg/L) in normal patients, multiply by ten, and determine total body tissue iron stores in grams. For example, the average ferritin (µg/L) in serum in normal adult males is 100, 100×10=1000 mg, which is the average adult male total body tissue iron store. The average ferritin (µg/L) in serum in adult females in the child-bearing years is 30, 30×10=300 mg, which is the average adult female (child-bearing years) body iron store. The female has ⅓ the body storage iron of the male because iron is lost monthly during menses.

Other standard serum iron measurements measure only the iron on Tf, which sticks out like a lollipop on the surface of the Tf molecule, plus low molecular weight iron (Borg, D. C., Handbook of Free Radicals and Antioxidants in Biomedicine, Volume I, CRC Press, Inc., 63–80 (1989)) such as might have been absorbed from iron succinate citrate (Aisen, P. et al., *Int. Rev. Exp. Path.*, 31:1–46 (1990)). Standard serum iron measurements do not measure the iron on ferritin, since that iron is buried in the core of the ferritin molecule. In this test, therefore, what is being measured is the iron that is being delivered to cells which need iron, since Tf is an iron-delivery protein. This elucidates no information about the stores of iron in the body.

Another test used is the measurement of stainable iron in the bone marrow or quantitative measurement of liver iron, which is the "gold standard" for assessing body iron stores. This method is impractical for routine screening due to it being an invasive test. Further, serum iron and iron binding capacity (Tf) measurements together with the resultant percent saturation of the iron binding capacity, e.g. of Tf, have been used, but are unreliable because they are affected by diurnal variation, and by any inflammation since Tf is a reverse acute phase reactant, and by drug ingestion such as vitamin C or alcohol. Accordingly, the present tests used to measure total body tissue iron stores are prone to inaccurate readings.

An example which highlights the drawbacks of the current tests is a measurement of total ferritin isolated from a serum sample in patients with inflammation or disease. Using the current tests, when there is acute serum apoferritin elevation in response to inflammation or cancer, the serum ferritin level does not closely mirror body iron stores such that multiplying the serum ferritin in µg/L by 10 gives a false reading with respect to the body iron stores in mg (Herbert V., et al., *Stem Cells*, 92:1502–1509 (1994)). Measurement of serum ferritin levels is generally accepted as the best non-invasive means of indirectly determining body iron stores only when the serum level of ferritin and the serum level of iron run in the same direction. This is because serum ferritin almost never accurately reflects body iron stores in any sick person, because serum ferritin=apoferritin+holoferritin, and, in any cell, reaction to illness or inflammation, for example, flu, pneumonia, rheumatoid arthritis, tonsillitis, heart disease, neoplastic diseases, renal failure or cancer, apoferritin rises, and iron quantity does not, and a reading of total ferritin provides inaccurate results.

Accordingly, measuring serum ferritin levels to determine total body tissue iron stores will lead to false results in a number of situations. A report that someone has a serum "ferritin" of 200 µg/l, for example, is meaningless with respect to the iron content of that ferritin. Some of the "ferritin" may be pure apoferritin with no iron, some may be holoferritin saturated with 4,500 atoms of iron per molecule of ferritin, and most of the holoferritin is probably somewhere between no iron content and 4,500 atoms of iron per ferritin molecule, In another example, serum "ferritin" levels in excess of 400 ng/ml are erroneously reported as defining iron overload by most clinical laboratories. Elevations in serum "ferritin" levels occur unrelated to iron stores in inflammatory conditions and in individuals with liver disease. In these situations serum "ferritin" is usually in excess of 400 ng/ml due to high apoferritin with no iron. Accordingly, the patient is diagnosed as having an iron overload when in reality there is only an apoferritin overload and iron levels may very well be normal. Further complicating the problem, many women ingest iron supplements, and this supplemental iron use has made iron/breast cancer risk studies especially difficult.

In a recent study (Adams, P. C., *Amer. J. of Hemat.*, 45:146–149 (1994)) the usefulness of serum ferritin, Tf iron and Tf saturation were evaluated for the detection of patients heterozygous for hemochromatosis versus normals. In heterozygotes, hepatic iron is 3 to 4 fold increased over normals. The whole group of heterozygotes had a significantly increased mean serum ferritin and Tf saturation compared with the whole group of controls. However, only 11% of individual heterozygotes had elevated serum ferritin levels and only 8.6% had elevated Tf saturation. Thus, currently available tests miss 90% of those at risk. Heterozygotes are at increased risk of developing cancer and heart attacks, especially in the presence of substances which release iron from ferritin, such as alcohol and/or vitamin C supplements. Over 40% of Americans take vitamin C supplements.

DESCRIPTION OF THE INVENTION

In accordance with a primary aspect of the present invention, there is provided a method for determining total body tissue iron stores.

In accordance with another aspect of the present invention, there is provided a method of measuring the quantity of ferritin-iron in a unit volume of body fluid.

In accordance with a further aspect of the present invention, there is provided a method for detecting altered levels of iron contained in total ferritin isolated from a unit volume of body fluid, as a risk factor for diabetes, impotence, cancer, heart disease, atherosclerosis and hepatic failure.

In accordance with still a further aspect of the present invention, there is provided a method for determining a genetic susceptibility to iron overload.

In accordance with yet another aspect of the present invention, there is provided a method for determining the presence of an inflammatory condition by determining ferritin protein levels in the case where iron status remains constant.

In accordance with still another aspect of the present invention there is provided a diagnostic assay which is non-invasive, easy to use and gives an accurate determination of total body tissue iron stores.

The present invention provides a method for determining total body tissue iron stores in a patient comprising isolating the total ferritin protein contained in a unit volume of a body fluid sample derived from the host, releasing the iron contained in the isolated total ferritin, measuring the quantity of ferritin-iron in the total ferritin and determining the total body tissue iron stores. The quantity of iron allows a direct determination of the quantity of ferritin which is holoferritin since only holoferritin contains iron. The present inventors have found that when measuring total body tissue iron stores, the amount of holoferritin and apoferritin must be measured to provide an accurate result. The amount of iron contained in the total ferritin protein isolated from a unit volume of body fluid from a patient is a measurement of circulating storage iron, which is relative to the amount of iron stored in the tissues. Therefore, by measuring the amount of iron, which is equivalent to holoferritin, in a unit volume of ferritin protein one skilled in the art can determine total body tissue iron stores.

The present inventors recognize that a crucial aspect of this determination is measuring the actual quantity of iron per unit volume of body fluid since this allows a determination of the number of units of holoferritin in the total ferritin isolated from the unit volume of body fluid. Holoferritin contains iron while apoferritin does not, therefore, a quantitation of iron allows a quantitation of holoferritin. Further since total ferritin is comprised of apoferritin and holoferritin only, quantitation of holoferritin allows an indirect quantitation of apoferritin.

The quantity of iron recovered from a unit volume of body fluid sample is measured as the number of atoms of iron and consequently may also be represented by nanograms (ng) iron, since a fixed number of atoms of irons comprised (1) ng of iron in the sample.

In a preferred embodiment of the present invention the unit volume of body fluid collected from the patient is one milliliter (1 ml). Any body fluid may be used to determine total body tissue iron stores since ferritin protein is a circulatory protein and has been found in all fluids of the body. Preferably, however, examples of body fluids which are acceptable for use in the method of the present invention include urine, blood, saliva, and liver and bone marrow samples. Most preferably, serum is used to collect a sample for use in the method of the present invention.

The amount of holoferritin may be expressed in different units by the method of the present invention. Holoferritin may be expressed as the average number of atoms of iron, or ng of ferritin-iron, stored in each molecule of ferritin protein. This amount of holoferritin gives an absolute figure for the average number of atoms of iron per molecule of ferritin protein. However, this only accurately measures iron stores when there is no inflammation, since the number of molecules of ferritin varies with respect to the presence or absence of inflammation. Therefore, in accordance with a preferred embodiment of the present invention, holoferritin is expressed as the total number of atoms of iron in the total number of molecules of ferritin protein in a unit of body fluid, in particular a one (1) ml body fluid sample. This gives the number of atoms of iron stored in all the molecules of ferritin in a one (1) ml sample of body fluid and accurately measures iron stores whether or not there is inflammation. An accurate determination of total body tissue iron stores is possible regardless of the presence of inflammation or disease, because the amount of holoferritin remains constant, and actual ng of recovered iron is being determined as opposed to quantity of ferritin protein. The presence of inflammation is not a confounding variable since it raises only the amount of apoferritin and not holoferritin. Examples of inflammation in the host are flu, pneumonia, rheumatoid arthritis, tonsillitis, heart disease and cancer.

Upon measuring the amount of iron in the total ferritin protein isolated from a specified volume, e.g. one (1) ml of body fluid the units of holoferritin in the total ferritin are determined as stated above. Since circulatory iron, or iron contained in holoferritin, is relative to iron stored in the body tissues, an exact measure of total body tissue stores can be determined, by multiplying the units of holoferritin, usually measured in micrograms, by a factor which depends on the size of the body fluid sample, for example it would be ten (10) if 1 ml of body fluid sample is used.

Alternatively, to calculate total body tissue iron stores from the amount of ferritin-iron, each nanogram (ng) ferritin-iron recovered per ml of body fluid sample represents approximately 10 ng of body storage iron. Thus, a serum ferritin-iron of 10 ng would represent approximately 100 ng of storage iron.

By measuring the number of atoms of iron, or ng of ferritin-iron in the total number of molecules of ferritin protein in a body fluid sample in accordance with the method of the present invention, a medical professional is able to accurately determine a patient's iron status. It is now possible to differentiate between patients with a normal iron content, patients who are iron-deficient, patients who have an iron-overload and patients with inflammation (or any disease which stimulates an increase in apoferritin). Prior to the present invention this differentiation was impossible. For example, if the total ferritin protein isolated from a body fluid sample is higher than normal but the iron content, measured by the method of the present invention, is lower than normal, it is indicative of an inflammation or disease since apoferritin has increased. The tests prior to the present invention, would only have alerted one skilled in the art that the "ferritin" protein has increased, which would cause an assumption that iron increased, when this in fact is not accurate.

On the other hand, if the total ferritin protein is average and the iron content is down the patient can be diagnosed accurately as having an iron deficiency. In another instance, if iron content is above normal the patient can be properly diagnosed as having iron overload due to being heterozygous for the iron-overload gene, since holoferritin will not increase for any reason other than iron-overload.

Referring to Table 1, a serum ferritin-iron below 10 ng/ml indicates iron insufficiency. The range of normal is a serum ferritin-iron between 10 and 35 ng/ml of serum. A serum ferritin-iron above 37 ng/ml of serum suggests iron excess and above 100 ng/ml is a positive diagnosis of iron excess. Because excess ferritin-protein, triggered by inflammation, may pull some iron out of the tissue, and thus may raise the absolute level of ferritin-iron per ml of serum above 37 ng/ml, patients with greater than 37 ng/ml of ferritin-iron preferably should also have the percent saturation with iron of their ferritin-protein determined. If the percent saturation is greater than 15%, the diagnosis is iron overload even if serum ferritin-iron does not exceed 100 ng/ml.

TABLE 1

Sequential Stages of Iron Status

| | (IRON EXCESS)** POSITIVE BALANCE | | ─── NORMAL ─── | ─── DEPLETION ─── | (IRON INSUFFICIENCY) NEGATIVE BALANCE | ─── DEFICIENCY ─── |
|---|---|---|---|---|---|---|
| | STAGE II | STAGE I | Normal | STAGE I | STAGE II | STAGE III | STAGE IV |
| | Iron Overload | Positive Iron Balance | Normal | Early Negative Iron Balance | Iron Depletion | Damaged Metabolism: Iron Deficient Erythropoiesis | Clinical Damage: Iron Deficiency Anemia |
| Iron Stores → | | | | | | | |
| Circulating Iron → | | | | | | | |
| Erythron Iron → | | | | | | | |
| RE Marrow Fe | 4+ | 3+ | 2–3+ | 1+ | 0–1+ | 0 | 0 |
| Transferrin IBC (μg/100 ml)† | <300 | <300 | 330±30 | 330–360 | 360 | 390 | 410 |
| Plasma Ferritin (μg/L)* | >300 | >150 | 100±60 | <25 | 20 | 10 | <10 |
| Iron Absorption (%) | >15 | 10–15 | 5–10 | 10–15 | 10–15 | 10–20 | 10–20 |
| Plasma Iron (μg/100 ml)† | >175 | >150 | 115 ± 50 | <120 | 115 | <60 | <40 |
| Transferrin Saturation (%)† | >60 | >45 | 35 ± 15 | 30 | 30 | <15 | <15 |
| Sideroblasts (%) | 40–60 | 40–60 | 40–60 | 40–60 | 40–60 | <10 | <10 |
| RBC Protoporphyrin | 30 | 30 | 30 | 30 | 30 | 100 | 200 |
| Erythrocytes | Normal | Normal | Normal | Normal | Normal | Normal | Microcytic/ Hypochromic |
| Serum Transferrin Receptors | Normal | Normal | Normal | Normal-High | High | Very High | Very High |
| Ferritin-iron (holoferritin) (ng/ml)‡ | Very High | High | Normal | Normal-Low | Low | Very Low | Very Low |

*Inflammation produces elevated ferritin, because ferritin is an acute phase reactant.
†Inflammation reduces transferrin (and the plasma iron on it), because transferrin is a reverse acute phase reactant.
‡Ferritin-iron is unaffected by inflammation, so it is reliable when ferritin, transferrin, and plasma iron are not.
**Randall Lauffer of Harvard and Joe McCord of Univ. Colorado-Denver hold that <u>any</u> storage iron is excessive because of its potential to promote excessive free radical generation. See V. Herbert et al. Stem Cells 1994; 12: 289–303. Most free radical injury is iron-related.
Dallman (pediatrician) definition of negative balance: less absorbed than excreted.
Herbert (internist) definition of negative balance: less absorbed than <u>needed</u>.

Prior to the present invention, it had to be assumed that a serum ferritin of 200 μg/L, in a patient who has a low serum iron and iron-binding capacity, contained a large content of apoferritin with no iron on it. Conversely, if a serum ferritin of 200 μg/L is accompanied by a high serum iron and iron-binding capacity, then it had to be assumed those 200 μg of serum ferritin are holoferritin and contain a large quantity of iron, perhaps even some ferritin saturated with 4500 atoms of iron per molecule of ferritin. Prior to the present invention is was impossible to determine the significance of the serum ferritin level.

In accordance with one advantage of the present invention, the presence of inflammatory conditions may also be diagnosed in a situation where iron status remains constant. In this situation, the presence of an inflammation causes an increase in ferritin protein, since it is an acute phase reactant. Accordingly, the detection of an increase in ferritin protein levels, by the methods of the present invention, allows a diagnosis of an inflammatory condition.

Assessing iron status is extremely significant. High body tissue iron stores have been strongly implicated in the pathogenesis of cancer, atherosclerosis, coronary artery disease, diabetes, impotence and hepatic failure among other disorders, including aging. The major group at risk for iron overload are those that are heterozygous for a gene which produces iron overload. Over 10% of American Caucasians have an HLA-linked gene for iron overload and about 30% of African-Americans have a non-HLA-linked gene for iron overload. HLA typing is not only too costly, but it does not identify Afro-American heterozygotes since their iron-overload gene is not HLA-linked. The importance of detecting iron overload is heightened by the potential further impact of two commonly used drugs, alcohol and vitamin C. About 40% of Americans consume 0.06–1 gram of vitamin C per day. Both of these commonly consumed drugs increase iron absorption and iron stores and release catalytic iron from ferritin.

A particular embodiment of the present invention measures nanograms ferritin-iron in a unit volume of serum ferritin, for example 1 milliliter (ml), which initially comprises recovering a known amount of serum from a patient, e.g. 1 ml, by methods known to those of skill in the art. Serum may be extracted from a patient and prepared for isolation of ferritin in a number of ways, for example, the serum may be isolated from a blood sample taken from a patient via a syringe. More specifically, the serum is prepared by allowing the blood to clot, spinning the blood at 3000×g for 10 minutes and separating the serum from the other blood components.

The ferritin is recovered by separating the serum ferritin from other serum proteins, which may be accomplished by a variety of methods known in the art, for example, acid extraction, ammonium sulfate or ethanol precipitation, anion or cation exchange chromatography or affinity chromatography. Preferably, however, immunological methods are used. These methods involve, for example, the use of an antibody directed against ferritin. The antibody may be directly bound to a substrate, for example polystyrene or polypropylene tubes or latex particles, or may be covalently bound to a substrate which is attached on the inside of polystyrene or polypropylene tubes or on the outside of latex particles. The prepared serum sample is then passed over the bound antibody in a standard solution, and the excess serum proteins are washed from the specific antibody-ferritin complex formed.

Antibodies for coupling to a substrate are suitably raised in any mammal, however, they are preferably raised in rabbits or sheep. For this purpose, 50 μg to 2 mg of ferritin are used. The primary immunization involves injecting a solution of ferritin with the addition of Freund's adjuvant. After some weeks test bleeds are taken from the animal to isolate the antibodies from the serum, either by precipitation with ammonium sulfate or by treatment with immunoabsorbants, for example, cyanogen bromide-activated SEPHAROSE 6B.

Production of antibodies suitable for use in the present invention from a rabbit comprises emulsifying a solution of 100 μg of ferritin in 1 ml of isotonic phosphate buffer at pH 7.4 with 1 ml of Freund's adjuvant and injecting the mixture intradermally at a number of sites.

Test bleeds are taken at 7 to 10 day intervals and the titer of the anti-serum is determined by immunodiffusion against ferritin. On obtaining a titer of 1:4, a bleed of 50 mls is taken. The bleeds are repeated at 14 day intervals until the titer falls below 1:4. All blood is allowed to clot and the serum is removed. The antibody thus isolated (immunogamma-globulin IgG) is bound to the substrate in the form of polystyrene tubes, polypropylene tubes or latex particles, the latter having a diameter of a few millimeters.

The antibody solution obtained is lyophilized and stored at 4° C. Subsequently, latex particles or polystyrene or polypropylene tubes are then washed in carbon tetrachloride and allowed to dry. The dry particles or tubes are contacted with hydrochloric acid and cooled to room temperature. The particles or tubes containing the antibody solution are stirred for 30 minutes and washed with distilled water until free of acid.

For isolating ferritin in serum, a substrate to which the anti-ferritin antibody (antibody directed against ferritin) is bound to, e.g. latex particles, is placed in a reaction tube (or in the case of a polystyrene or polypropylene tube, the antibodies are already bound to the inside of the tube), diluted with normal saline and a portion removed and incubated for several hours, preferably overnight, at a temperature of about 1° to 10° C., preferably 4° C., with 1 ml of patient's serum, and 1–2 ml of borate buffer, preferably having a pH of between 8 and about 9.2. From 0.2 to 1.0 weight percent of bovine serum albumin may also be added to the incubation solution. The substrate-antibody-ferritin complex may then be washed with between 1–5 ml of the initial washing buffer.

The tubes may then be centrifuged and the serum aspirated. The tubes may the be washed with iron-free water followed by centrifugation and aspiration of the supernatant and dried overnight.

After the ferritin has been precipitated and concentrated, the iron in the ferritin is extracted and released. The iron is liberated by a number of methods, including reducing the ferritin molecule with reducing agents and the use of solubilizing agents to digest the ferritin protein shell and liberate iron out of the shell. Any reducing agents may be used, including sulphydryl compounds, preferably, however, the iron is freed from the ferritin with hydrazine.

The ferritin molecules may also be digested using acid and heating to release ferritin-iron.

As stated previously, the iron is reduced such that the iron can now freely pass out of the ferritin molecule and be measured. Ferric iron, $Fe^{3+}$, is unable to be released from the ferritin molecule and, accordingly, can not be measured. When the ferric iron is reduced to ferrous iron, $Fe^{2+}$, the iron in each ferritin molecule is released and moves out of the ferritin molecule and is, therefore, free of the ferritin molecule and capable of being measured.

The liberated free iron may be measured by methods which depend upon the catalytic activity of free iron. For example, by the catalytic generation of thiobarbituric acid reactive material generated by the action of free iron on bleomycin complexed with DNA. Bleomycin is a glycopeptidic antibiotic used in the treatment of cancer whose major effect is the degradation of DNA. One postulated mechanism of action is that it binds to DNA and then is activated to form free radicals in the presence of $Fe^{2+}$.

For example, the released iron is measured by the colorimetric method which involves reacting a colorimetric agent with the sample solution after adjustment to an acidic pH with the addition of saturated sodium acetate and measuring the change in absorbance at 534 nm. The colorimetric assay may use various colorimetric agents, such as ferrozine. Preferably, however, the colorimetric agent is bathophenanthroline, and in an even more preferred embodiment it is bathophenanthroline sulfonate.

Iron may also be determined by removing a portion of the acid digest and assaying this aliquot directly in an atomic absorption spectrophotometer with a graphite furnace under an argon atmosphere.

It should be readily apparent to those of skill in the art from the teachings herein, that other body fluids may be substituted for the examples given which use blood serum as the body fluid for determining total body tissue iron stores.

Having now generally described the invention, the same will be more readily understood through reference to the following examples which are provided by way of illustration only and are not intended to be limiting of the present invention.

EXAMPLE 1

Measurement of Iron Content in 1 ml of Serum Ferritin

Step 1. Preparation and Concentration of Serum Ferritin with Antibody 1.1 Precipitation of Serum Ferritin with Rabbit Anti-human Serum Ferritin A 1:1000 dilution of 7 mg/ml rabbit polyclonal anti-human anti-ferritin antibody (Accurate Chemical and Scientific, Westbury, Long Island) is delivered in a 2 ml volume of 0.2M $NaHCO_3$, pH 9.2 to 12×75 polystyrene tubes. The tubes are rotated for 90 minutes at room temperature on an automated rotator at a 45° angle. The antibody excess is removed and the tube is washed with 2 ml of 4.5 g/L NaCl pH 8.2 containing 1 mg/ml of bovine albumin followed by a wash with chelexed distilled water (Chelex 50:100 mesh, Sigma Chemical Company, St. Louis, Mo.). The tubes are then incubated with samples of serum diluted in 2 ml of the initial washing buffer. The tubes are incubated overnight at 4° C.

1.2 Precipitation of Ferritin with Antiferritin Antibody Bound to Latex Particles Monoclonal antiferritin antibody-coated latex particles are used. Approximately 100–500 µl of serum is incubated for 30 minutes (with gentle mixing) at 25° C. with 50–200 µl of mouse monoclonal antiferritin coated particles. The suspension is spun at 4000 times g for 10 minutes and washed with .1M $NaHCO_3$ at pH 8.2 washing buffer and spun again to separate free and transferrin bound iron.

1.3 Precipitation of Ferritin with Rabbit Anti-Human Serum Ferritin Coated on Polypropylene Tubes The method is similar to Example 1, however, the tubes are first treated with a solution of 1% glutaraldehyde at 56° C. for 1 hour in order to facilitate binding of antibody to the tube.

Step 2. Release by Solubilization and Reduction of Ferritin Iron 2.1 Separation of Antibody Bound Ferritin From Latex Particles or Tubes The ferritin-antibody complex may first be separated from the latex particles by incubation for 15 minutes at 37 degrees centigrade with a detergent. A 5 percent solution of polyoxyethylene sorbitan monolaurate (TWEEN 20) is used. 0.25 ml is added to the spun and washed latex particles from the incubation detailed in 1.2 above. Separation of the ferritin from the latex particles provides a cleaner sample for the colorimetric reaction for the determination of iron.

The detergent can similarly be added to remove the ferritin from the coated tubes and thus concentrate it in a small volume.

2.2 Hydrazine Reduction (to Release the Iron From the Ferritin)

Hydrazine is added to the ferritin that has been separated in step 2.1 above, either from latex particles or from tubes, in a final concentration of 1.25%. It is reacted at 25 degrees centigrade for 10 minutes.

2.3 Protein Precipitation, Solubilization and Reduction of Iron

Any remaining ferritin-bound iron is liberated through acidification by addition of 0.25 ml of a solution of 1M hydrochloric acid, 10% trichloroacetic acid and 3% thioglycolic acid. This is incubated for 60 minutes at 70 degrees centigrade. Proteins are hydrolyzed or precipitated by this step.

Step 3. Measurement of Iron 3.1 Bathophenanthroline Assay

The concentrating of serum ferritin by immunological techniques described above in Step 1, and the release by solubilization and reduction of ferritin bound iron described in Step 2, is now followed by the measurement of the ferritin iron by a colorimetric method. A microcuvette is used that enables that measurement of color change in 0.25–0.5 ml samples. The extinction coefficient for bathophenanthroline is 22,140 at 534 nm. The combination of immunological techniques for concentrating the ferritin, the liberation of ferritin iron and the microcolorimetric method enables the reliable quantitation of as little as 10 ng of iron/sample.

The chromogen solution is comprised of 1.5M sodium acetate containing 0.025% bathophenanthroline sulfonate with a pH of 4.5. It is prepared fresh. The chromogen solution is added in equal volume to the sample solution and allowed to react for 10 minutes at 25 degrees centigrade. A standard of $Fe^{2+}$ (from ferrous chloride) dissolved in the acid solution detailed in part 2.3 above is used. Standards of 0, 5, 10, 20, 40 and 80 ng of iron are used. The absorbance is measured at 534 nm and the iron content of samples calculated from the standard curve prepared from the iron standards.

3.2 Bleomycin-DNA Assay

Following release and solubilization from ferritin, the ferritin iron may be measured by other assays such as the bleomycin-DNA assay. Production of a thiobarbituric acid reactive product results from the reaction of DNA and bleomycin in the presence of solutions containing traces of iron salts. 0.5 ml of calf thymus DNA (1 mg/ml) is mixed with 0.05 ml of bleomycin sulphate (1 mg/ml), 0.1 ml of 50 mM $MgCl_2$, 0.05 ml of 10 mM HCl, 0.1 ml of 70 mg/ml ascorbate and 0.1 ml of sample. After incubation at 37° for 2 hours the reactions are stopped by the addition of EDTA (1 ml of 0.1M) and mixed with an equal volume of 1 ml of 1% w/v thiobarbituric acid, heated at 100° C. for 15 minutes, cooled and the chromogen read at 534 nm. Samples are compared to a standard curve using ferric chloride.

EXAMPLE 2

Measurement of Serum Ferritin-Iron

Step 1. Immuno-precipitation and Concentration of Ferritin

Rabbit anti-human ferritin polyclonal antibody (7 mg/ml) was purchased from Accurate Scientific, Westbury, N.Y. The antibody was diluted 0.1–10 ml with normal saline. 50 lambda was then mixed with and incubated at pH 8.2 overnight at 4° C. with 0.025 ml of Repligen IPA 400 immobilized rProtein A cross linked to agarose beads (Repligen Corp., Cambridge Mass.) in a polypropylene tube. The antibody bound to agarose was stored at 4° C. in the individual tubes until used. 2 ml of serum is added to each tube, incubated 2 hours at room temperature with gentle rocking, and then allowed to stand overnight at 4° C.

Step 2. Washing to Remove Other Iron-containing Proteins

The following morning the tubes are spun at 5000 g and the serum aspirated. The beads are washed twice with 2 ml aliquots of iron-free water followed by spinning at 5000 g and aspiration of the supernatant. The tubes are then dried in a 37° C. dryer overnight.

Step 3. Digestion

To each tube 0.2 ml of $HNO_3$ (3N) is added, vortexed and heated for 2 hours at 75° C. in a waterbath, 30 min to 1 hour is sufficient. All material is dissolved at this point.

Step 4. Determination of Iron

10 Lambda aliquots of the nitric acid digest are assayed directly in an Atomic Absorption Spectrophotometer (Perkin Elmer Model 5000) with a graphite furnace (Model HGA 2200), under an argon atmosphere. Absorbance is measured at 2.483 nm. The sample is dried at 100° C. for 50 seconds (ramp time 25 seconds), charred at 1500° C. for 50 seconds (ramp time 20 seconds) and atomized at 2500° C. for 7 seconds. The sensitivity of the assay was approximately 1 ng Fe.

Numerous modifications and variations of the present invention are possible in light of the above teachings and, therefore, within the scope of the appended claims, the invention may be practiced otherwise than as particularly described.

We claim:

1. A process for evaluating total body tissue iron stores in a patient comprising:

releasing iron contained in ferritin protein isolated from a unit volume of body fluid sample recovered from the patient;

measuring the released iron; and evaluating the total body tissue iron stores in the patient by comparing the amount of measured released iron per unit volume to a normal range for ferritin iron per unit volume.

2. The process of claim 1 further comprising measuring the percent saturation of iron in the isolated ferritin protein and further evaluating the total body tissue iron stores based on said percent saturation.

3. The process of claim 1 wherein the body fluid sample is serum.

4. The process of claim 1 wherein the ferritin protein is isolated by immunoprecipitating the ferritin protein from the body fluid sample with an anti-ferritin antibody bound to a solid support, wherein said supported anti-ferritin antibody was prepared by incubating the anti-ferritin antibody with the solid support at a pH of about 8.2.

5. The process of claim 4 wherein the anti-ferritin antibody is a rabbit anti-ferritin polyclonal antibody.

6. The process of claim 4 wherein the solid support is agarose beads.

7. The process of claim 1 wherein isolating the ferritin protein includes immunoprecipitating the ferritin protein with an anti-ferritin antibody covalently bound to a solid support, wherein said supported anti-ferritin antibody was prepared by incubating the anti-ferritin antibody with the solid support at a pH of about 8.2.

8. The process of claim 7 wherein the anti-ferritin antibody is a mouse anti-ferritin monoclonal antibody.

9. The process of claim 7 wherein the anti-ferritin antibody is a rabbit anti-ferritin polyclonal antibody.

10. The process of claim 7 wherein the solid support is agarose beads.

11. The process of claim 8 wherein the solid support is latex particles.

12. The process of claim 1 wherein releasing the iron contained in the ferritin protein comprises contacting the ferritin protein with a reducing agent to convert ferric iron to ferrous iron.

13. The process of claim 12 wherein the reducing agent is hydrazine.

14. The process of claim 1 wherein releasing the iron contained in the ferritin protein comprises contacting the ferritin protein with an acid and heating the resulting solution.

15. The process of claim 14 wherein the acid is nitric acid.

16. The process of claim 1 wherein measuring the iron comprises reacting the released iron with a bathophenanthroline compound, measuring the absorbance at 534 nanometers, and comparing the measured absorbance to a standard curve prepared from samples containing a known amount of iron.

17. The process of claim 16 wherein the bathophenanthroline compound is bathophenanthroline sulfonate.

18. The process of claim 17 wherein the pH of the bathophenanthroline sulfonate is adjusted to 4.5.

19. The process of claim 1 wherein the released iron is measured by atomic absorption spectrophotometer with a graphite furnace under an argon atmosphere.

* * * * *